(12) United States Patent
Akutsu et al.

(10) Patent No.: US 6,409,382 B1
(45) Date of Patent: Jun. 25, 2002

(54) MOBILE X-RAY APPARATUS

(75) Inventors: Koji Akutsu, Nara; Tatsuya Araki, Ohmihachiman; Kimihiro Takahama, Kyoto; Toshio Kadowaki, Kyoto; Hajime Takemoto, Mukou, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/818,578

(22) Filed: Mar. 28, 2001

(30) Foreign Application Priority Data

| Mar. 28, 2000 | (JP) | 2000-087764 |
| May 23, 2000 | (JP) | 2000-150755 |
| Feb. 20, 2001 | (JP) | 2001-42631 |

(51) Int. Cl.$^7$ .................................. H05G 1/02
(52) U.S. Cl. .................. 378/198; 378/197; 378/114
(58) Field of Search .............. 378/193, 197, 378/198, 114, 117

(56) References Cited

U.S. PATENT DOCUMENTS 5,388,142 A * 2/1995 Morris ........................ 378/198
5,499,284 A * 3/1996 Pellegrino et al. ........... 378/198
6,131,690 A * 10/2000 Galando et al. ............. 180/411

* cited by examiner

Primary Examiner—Robert H. Kim
Assistant Examiner—Jurie Yun
(74) Attorney, Agent, or Firm—Radar, Fishman & Grauer, PLLC (57) ABSTRACT

A mobile X-ray apparatus for a circuit examination, which includes an X-ray tube with a collimator, a mobile base having a pair of driven wheels, a holder attached and movable to the base, the holder holds the X-ray tube. A motor driver is disposed in the base which drives the wheels. An operation handle bar is disposed in the base providing a signal for driving the motor driver. An input means, separated from the handle bar, provides a signal for driving the motor driver slightly. A controller controls the motor driver according to the signal from the handle bar or the input means.

23 Claims, 5 Drawing Sheets

MOBILE X-RAY APPARATUS

BACKGROUND OF THE INVENTION

1. Field of the Invention

This invention is related to a mobile X-ray apparatus for a circuit examination.

2. Description of the Related Art

Figure 4A:
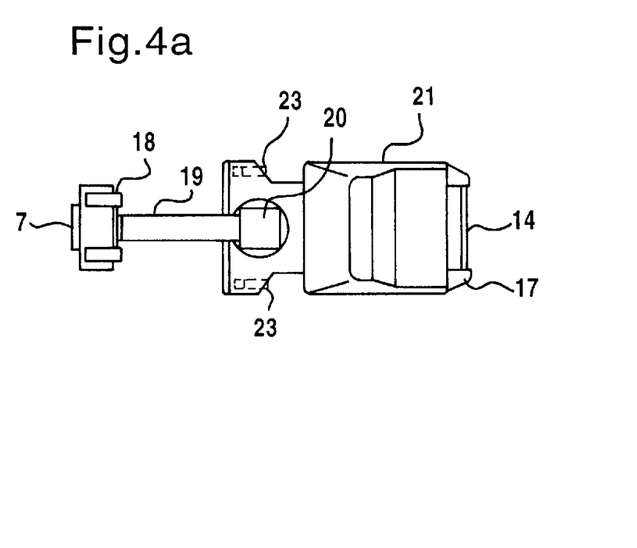
FIG. 4 is a schematic view of a mobile X-ray apparatus for a circuit examination in an embodiment of this invention.
Figure 4B:
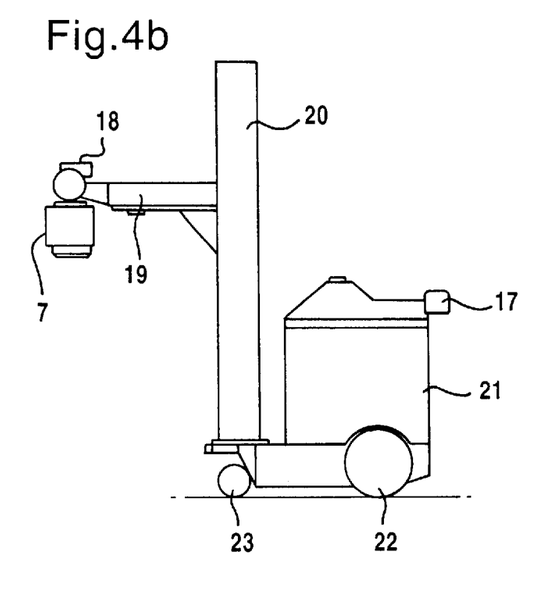
Figure 4C:
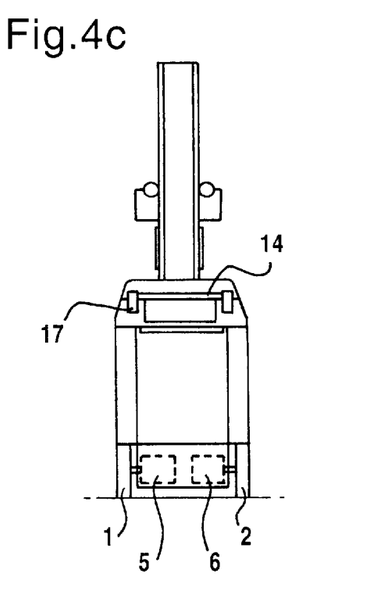

A mobile X-ray apparatus for a circuit examination by a doctor in a conventional cordless condenser type is shown in FIG. 4a–FIG. 4c. FIG. 4a is an elevational view, FIG. 4b is a side view, and FIG. 4c is a plane view thereof. This apparatus has an X-ray tube 18, an arm 19 holding the X-ray tube 18, a collimator 7, a truck 21, a column 20 which is rotatably mounted on the truck 21, a up-down motion part which moves the arm 19 up and down along the column 20. The truck 21 has a pair of pivotable front wheels 23 and a pair of unpivotable rear wheels 22 (a right wheel 2 and a left wheel 1). This apparatus also has a X-ray controller in the truck 21. A lower disposed drive motors (a right motor 6 and a left motor 5) move the truck 21 forward or backward corresponding to manipulating an operation handle bar 14 forward and backward. The operation handle bar 14 is attached to the handle holding base 17 disposed in the truck 21.

The arm 19 has a structure for supporting and rotating the X-ray tube 18. The arm 19 also has a structure for horizontally extending and shortening itself. This apparatus is structured to keep its balance when the arm 19 moves up and down along the column 20. Therefore, the X-ray irradiation aperture of the X-ray tube 18 can be target in all directions and positions, according to a target part of an examined body.

Weight of this mobile X-ray apparatus for a circuit examination could be more than 450 kg. In that case, it is very difficult to move the truck 21 without power assist. The truck 21 generally has the rear wheels 22, which are not pivotable, and the front wheels 23 which are pivotable like casters. The rear wheels 22 are generally driven by drive motors (the right motor 6 and the left motor 5).

The truck 21 has an internal power supply with a car battery and an inverter, a high voltage transformer, a condenser, and a control circuit (not shown). The internal power supply provides 100–120V and 60 Hz power through the control circuit. An automatically programmed one-touch system is frequently used for photographing operation.

Rubber tires are used for the truck 21, and the truck 21 is designed such that it can freely move into and out of a patient's room, an operation room or an elevator, for example. Further, the truck 21 includes a braking system, a cassette box, and accessory devices (also not shown).

It is important for a circuit examination by a doctor for the mobile X-ray apparatus to be small and light weight, and have good mobility so that the mobile X-ray apparatus can be moved to a bedroom, a technician room, an operation room, a children room, an X-ray room, an infant room, or the like in a hospital so as to take an X-ray photographing easily at these sites.

Figure 5:
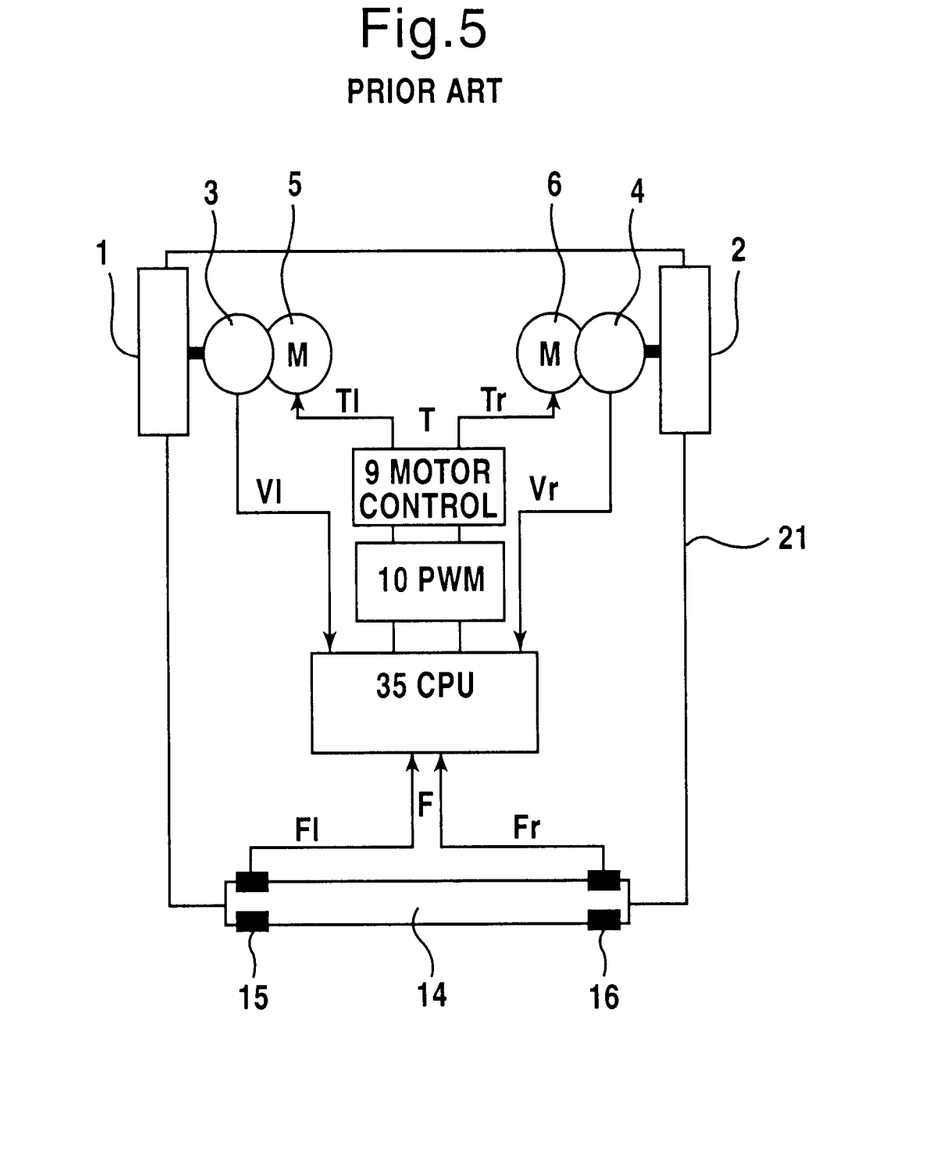
FIG. 5 is a schematic block diagram of the conventional mobile X-ray apparatus.

A block diagram for controlling the mobile X-ray apparatus is shown in FIG. 5. The left wheel 1 and right wheel 2 shown in the upper part of the diagram are driven by the left motor 5 and the right motor 6, respectively. The left motor 5 and the right motor 6 are independently controlled by the motor drive circuit 9. The PWM control circuit 10 carries out a switching control of the motor drive circuit 9 by pulse width modulation. The duty ratio in the switching control is controlled through signals from the CPU 35. When an operator manipulates the operation handle bar 14 of the truck 21 back and forth, signals from the left force sensor 15 and the right force sensor 16 attached to each end of the operation handle bar 14 are independently provided, as a left input Fl and a right input Fr to the CPU 35, respectively. On the other hand, signals of the left wheel rotation speed Vl and the right wheel rotation speed Vr from the left encoder 3 and the right encoder 4 which are placed at each spindle of the left wheel 1 and the right wheel 2 are provided to the CPU 35. The CPU 35 provides the PWM control circuit 10 with the duty width control signal in switching control corresponding to a back and forward input signal Ft(Fl, Fr) from the left force sensor 15 and right force sensor 16, and also a velocity signal Vt(Vl, Vr) from the left encoder 3 and the right encoder 4. The PWM control circuit 10 controls the motor drive circuit 9, and the motor drive circuit 9 controls the rotation speed of the left motor 5 and the right motor 6. The left force sensor 15 and right force sensor 16 include a flexible spring member, a Hall Effect Sensor, and a linear magnet, respectively.

The operation handle bar 14 is attached to the truck 21 through stiff but flexible spring members. The two spring members at each end of the truck 21 are hard leaf springs which make it possible to move the operation handle bar 14 back and forth a small distance corresponding to a force put on the operation handle bar 14 by its forward and backward operation. A pair of linear magnets (not shown) are attached to both ends of the operation handle bar 14.

A pair of Hall Effect (not shown) sensors are attached to the truck 21, corresponding to the linear magnets. The Hall Effect sensors are connected to a power supply (not shown in the Figures). When the Hall Effect sensor is placed at the center of the magnet, its output signal is zero level. On the other hand, when the Hall Effect sensor deviates from the center of the magnet, its output signal changes linearly between the positive maximum value and the negative maximum value. Polarity of the sensor signal corresponds to the direction of the displacement of the operation handle bar 14. Magnitude of the sensor signal is in proportion to this displacement.

The spring members make it possible to move easily the operation handle bar 14 by manipulating it back and forth and also to move it rapidly back to the neutral position just by release it.

As described above, the conventional mobile X-ray apparatus has a structure having both ends of the operation handle bar 14 being supported by laminated springs, and also that the operation handle bar 14 goes back at the neutral position, supporting its gravitative load by the laminated springs, when no operation force is added. Operation force is detected by detecting a position of magnets attached to the operation handle bar 14 by using the Hall Effect sensors. Operation force may also be detected by using strain gages stuck on the laminated springs supporting the operation handle bar 14. The apparatus is structured to move at a speed depending on operation force detected.

To use the device, an operator may push the apparatus at the operation handle bar 14 and move the apparatus to a bed side with power assist. The operator releases the operation handle bar 14 to stop the device and moves to the X-ray tube 18. Beside the X-ray tube 18, the operator may move it vertically up and down along the column 20, rotate it, and extend or shorten the arm 19 horizontally so as to aim the X-ray radiation aperture of the collimator 7 at the target part of the patient.

When a position of the X-ray tube 18 is adjusted, it may be impossible in some cases to aim it at the specified position without moving the whole apparatus again. When that happens with the conventional apparatus, the operator must go back near the apparatus body and manipulate the operation handle bar 14 again to adjust the position of the apparatus. This operation can take a long time to adjust the position of the X-ray tube 18 and also reduces examination efficiency.

Accordingly, the present invention has been made to solve the aforementioned problems. One object of the present invention is to provide a mobile X-ray apparatus for a circuit examination which makes it possible to adjust the position of the X-ray tube 18 rapidly when moving the apparatus to a position in order to photograph a patient.

SUMMARY OF THE INVENTION

To achieve the above objects, the present invention provide a mobile X-ray apparatus for a circuit examination, which includes an X-ray tube with a collimator, a mobile base having a pair of driven wheels, a holder attached and movable to the base, the holder holds the X-ray tube. A motor driver is disposed in the base which drives the wheels. An operation handle bar is disposed in the base providing a signal for driving the motor driver. An input means, separated from the handle bar, provides a signal for driving the motor driver slightly. A controller controls the motor driver according to the signal from the handle bar or the input means.

The input means may be placed at a part which can move independently from the mobile base. The part may be the collimator. The part may be the X-ray tube. The part may also be the holder.

The controller may stop the motion of the mobile base when receiving a signal from the handle bar during the receiving of a signal from the input means.

The controller may stop the motion of the mobile base when receiving a signal from the input means over a predetermined time. The predetermined time is, preferably, 10 seconds to 20 seconds.

DESCRIPTION OF THE PREFERRED EMBODIMENTS

Figure 1:
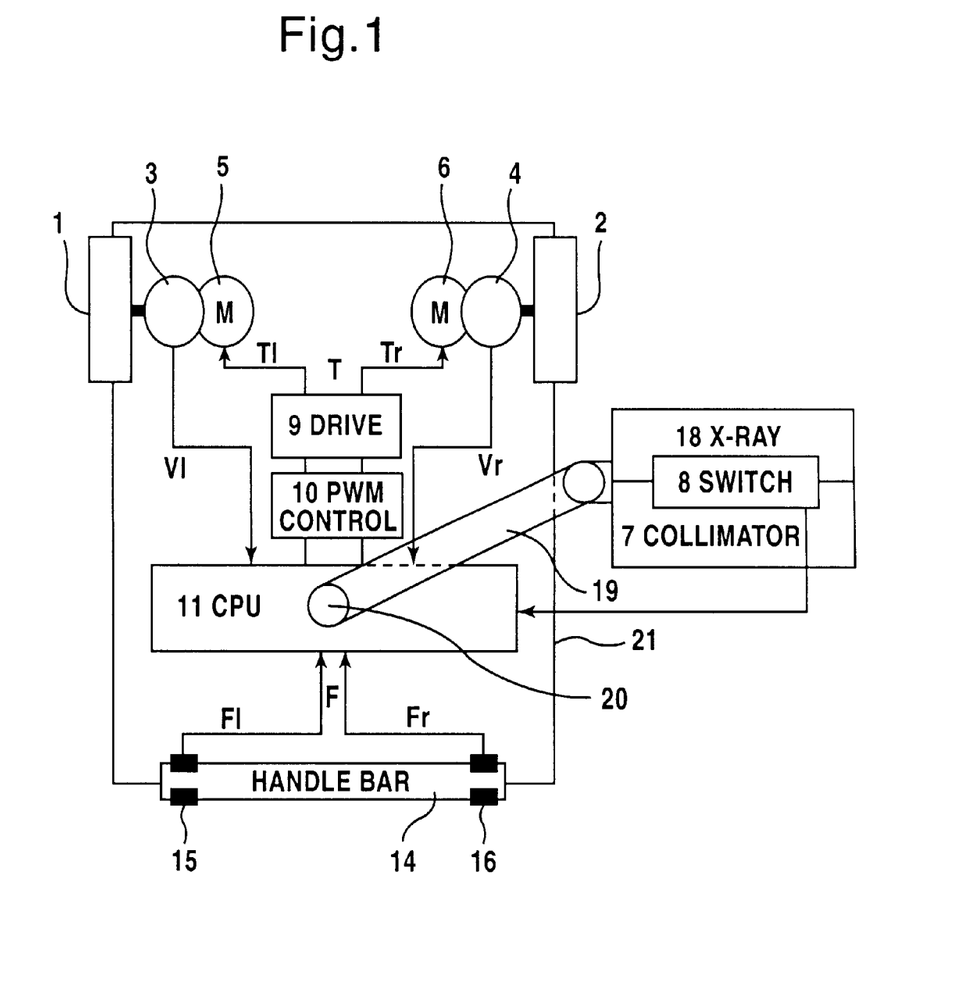
FIG. 1 is a schematic block diagram of a mobile X-ray apparatus for a circuit examination in an embodiment of this invention.

An embodiment of the present invention is described referring to FIG. 1. FIG. 1 is a schematic block diagram of a mobile X-ray apparatus. This apparatus has a pair of driven wheels (the left wheel 1, the right wheel 2), attached to a truck 21, which are driven respectively. The truck 21 has an operation handle bar 14 at both ends of which a left force sensor 15 and a right force sensor 16 are attached respectively. The left force sensor 15 and the right force sensor 16 detect each operation force put on both ends of the operation handle bar 14 respectively. The left wheel 1 and the right wheel 2 are connected to the left motor 5 and the right motor 6 respectively. The left encoder 3 and the right encoder 4, which are attached to each spindle of the left wheel 1 and the right wheel 2, detect each rotation speed thereof. A micro motion switch 8 for moving the apparatus slightly is attached to the side of an X-ray tube 18 or a collimator 7 at the end of an arm 19 which are attached to a column 20. A CPU 11 receives the input signal F(Fl, Fr) from the left force sensor 15 and the right force sensor 16, the wheel rotation speed input signal V(Vl, Vr) from the left encoder 3 and the right encoder 4, and a signal from the micro motion switch 8, and provides a PWM control circuit 10 with a duty width control signal. The PWM control circuit 10 carries out pulse width control of a motor drive circuit 9. The motor drive circuit 9 controls the left motor 5 and the right motor 6.

One difference between this apparatus and the conventional apparatus is that this apparatus has the micro motion switch 8, for moving the apparatus slightly, at very low speed compared to a speed by manipulating the operator handle bar 14. The micro motion switch 8 is attached to the side of the X-ray tube 18 or the collimator 7 at the end of the arm 19 attached to the column 20.

The micro motion switch 8 may be set on parts other than the operation handle bar 14, such as the X-ray tube 18 or the collimator 7, which travels off the apparatus body. Therefore, an operator can move the apparatus slightly through manipulating the micro motion switch 8 without manipulating the operation handle bar 14, and adjustment of the X-ray tube 18 can be carried out rapidly since the operator does not have to go back to the operation handle bar 14 to move the apparatus.

In an embodiment shown in FIG. 1, the micro motion switch 8 is set at the side of the collimator 7, and the apparatus moves slightly backward and forward by inclining the micro motion switch 8 forward or backward. One of the left wheel 1 and the right wheel 2 rotates by inclining the micro motion switch 8 left or right, and the apparatus may moves slightly along a circular line in the left or right direction.

The apparatus may be configured to stop automatically when the micro motion switch 8 is kept inclined in a direction for a given period of time. In this configuration, the apparatus can not be moved a long distance by using the micro motion switch 8, but repeating the operation of inclination of the micro motion switch 8 at intervals makes it possible to move the apparatus a long distance.

When the operation handle bar 14 is operated mistakenly during operation of the micro motion switch 8, the apparatus may be configured to stop automatically. The micro motion switch 8 may be a handle type for operation by inclining. The micro motion switch 8 may be also a separate button type (including a touch film type button).

The CPU 11 controls the PWM control circuit 10 to move the apparatus at a constant speed by operation of the micro motion switch 8. However, the CPU 11 may control the PWM control circuit 10 to move the apparatus at a variable speed in proportion to the amount of inclination of the micro motion switch 8 (or in the case of a button, the number of times it is pressed, or how hard it is pressed, etc.). The CPU 11 may also control the PWM control circuit 10 to move the apparatus at a speed according to a force put on the micro motion switch 8.

The operation handle bar 14 may be attached to the truck 21 through spring members which are relatively stiff (hard) but flexible. Two spring members connected respectively to both sides of the truck 21 may be, for example, hard laminate springs. These spring members make it possible to displace the operation handle bar 14 slightly according to an operation force put on the operation handle bar 14, generated by pushing or pulling it.

A pair of linear magnets which move with the operation handle bar 14 are attached to both ends thereof. On the other hand, a pair of Hall Effect sensors (parts of the left force sensor 15 and the right force sensor 16) may be attached to the truck 21 corresponding to the linear magnets.

When each Hall Effect sensor is placed at each center of the linear magnets, its output signal is zero level. When each Hall Effect sensor deviates from each center of the linear magnets, its output signal changes linearly between a positive maximum value and a negative maximum value.

Figure 2:
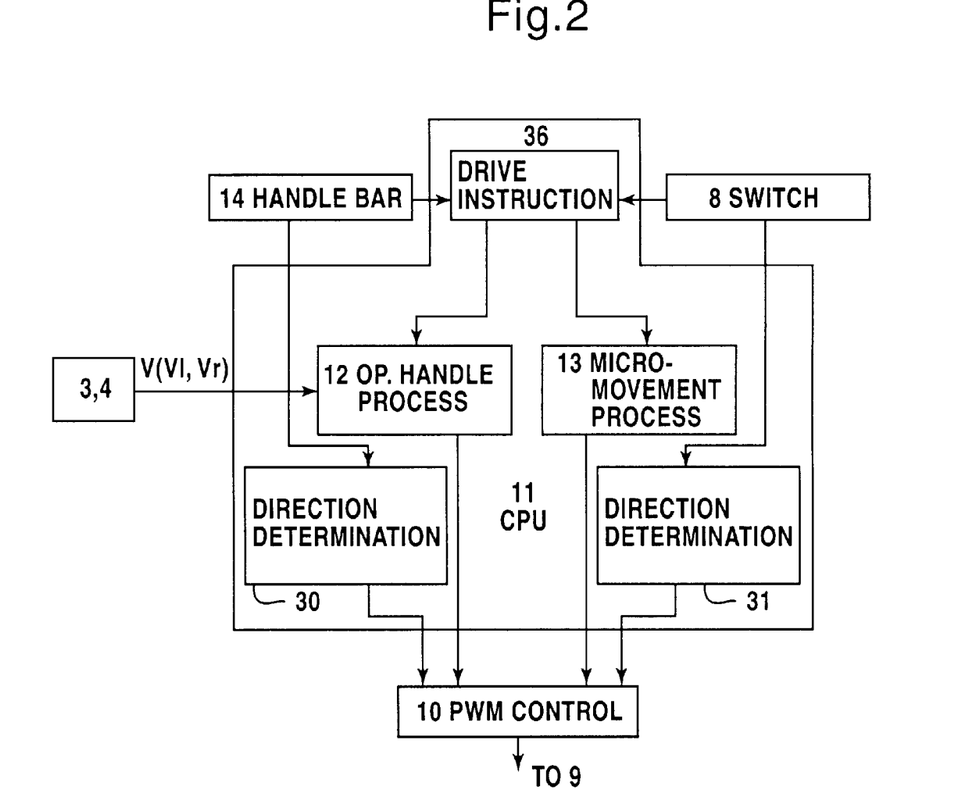
FIG. 2 is a schematic block diagram of a CPU driving circuit of a mobile X-ray apparatus for a circuit examination in an embodiment of this invention.

The explanation has been made for operation of the CPU 11. FIG. 2 shows a circuit of the CPU 11 which receives signals from the micro motion switch 8 and the operation handle bar 14. The CPU 11 receives signals, as the left input Fl and the right input Fr, generated from the left force sensor 15 and the right force sensor 16, according to manipulation of the operation handle bar 14. The drive instruction circuit 36 determines the absolute value Fla and Flb of the left input Fl and the right input Fr from these signals. The direction determination circuit 30 determines each code of the left input Fl and the right input Fr from these signals, and then determines each rotation direction of the left wheel 1 and the right wheel 2 to provide the PWM control circuit 10 with their direction information.

The left encoder 3 and the right encoder 4, which are attached to spindles of the left wheel 1 and right wheel 2 and detect rotation speeds thereof respectively, provide the CPU 11 with the wheel rotation speed input signal V(Vl, Vr).

The operation handle process circuit 12 of the CPU 11 determines the absolute value Vla and Vlb from signals of the left rotation speed Vl and the right rotation speed Vr. The operation handle process circuit 12 also determines the absolute value Tla, and Tra of each element of the torque signal T(Tl, Tr) which the motor drive circuit 9 should output by the following formula.

$Tla = \alpha(Vla) \cdot Fla$ $Tra = \alpha(Vra) \cdot Fra$

Figure 3:
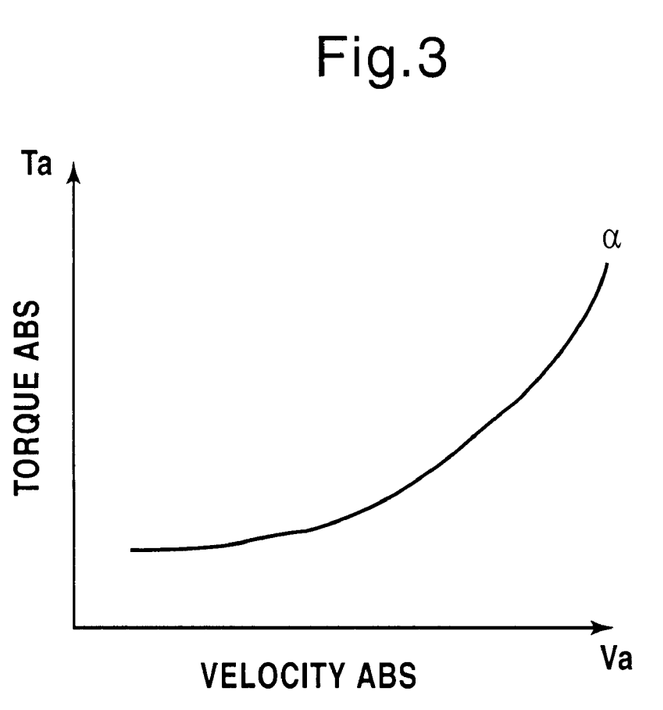
FIG. 3 is a view of a compensation function in an embodiment of this invention.

The above $\alpha$ is a compensation function, as shown in FIG. 3. In FIG. 3, Va is the absolute value of velocity and Ta is the absolute value of torque. The compensation function a compensates the output torque determined by the left input Fl and the right input Fr according to each rotation speed of the left wheel 1 and the right wheel 2 because of the nature that the more the speed increases, the less the torque decreases.

The PWM control circuit 10 drives the left motor 5 and the right motor 6 through the motor drive circuit 9 using each output of the direction determination circuit 30 and operation handle process circuit 12 so that the left motor 5 and the right motor 6 drive the left wheel 1 and the right wheel 2 at the determined torque T(Tl, Tr).

The operator moves the apparatus to a place for photographing through manipulation of the operation handle bar 14. Then the operator leaves the operation handle bar 14 and moves to the collimator 7. The operator then aims the irradiation aperture of the collimator 7 of the X-ray tube 18 at the target part of a patient to be examined.

Precise adjustment of the collimator 7 can be carried out, moving the apparatus slightly by manipulation of the micro motion switch 8 attached to the side of the collimator 7 (or the X-ray tube or an appropriate position for simultaneous positioning of the collimator 7 and the apparatus). Manipulation of the micro motion switch 8 provides the drive instruction circuit 36 and the direction determination circuit 31 of the CPU 11 with a signal by which the direction determination circuit 31 determines whether to move forward, move backward, turn left, or turn right. When the apparatus stands, both rotation speeds of the left wheel 1 and the right wheel 2 are zero. The micro movement process circuit 13 of the CPU 11 outputs to the PWM control circuit 10 the duty width control signal which makes the torque output of the motor drive circuit 9 to be Ta which is $\beta$ ($\beta$ is a constant). The direction determination circuit 31 of the CPU 11 determines which direction the micro motion switch 8 is manipulated. When the direction determination circuit 31 recognizes that a direction of the manipulation of the micro motion switch 8 is forward or back, it outputs to the PWM control circuit 10 a signal which indicates to drive both wheels forward or back. When the direction determination circuit 31 recognizes that direction of the manipulation of the micro motion switch 8 is left or right, it outputs to the PWM control circuit 10 a signal which indicates to drive the left wheel 1 or the right wheel 2, respectively.

The PWM control circuit 10 controls the motor drive circuit 9 to drive both or one of the left motor 5 and the right motor 6 at the determined torque (Ta=$\beta$) and in the determined direction based on signals from the CPU 11.

When the micro motion switch 8 is kept inclined in a direction for a given time, for example 10 seconds to 20 seconds, the drive instruction circuit 36 stops output of its signal and movement of apparatus for safety until manipulation of the micro motion switch 8 stops once. In this configuration, using the micro motion switch 8 will not allow the apparatus to move a long distance at a time, but repeating the operation of inclination of the micro motion switch 8 at intervals makes it possible to move the apparatus for a long distance.

When the operation handle bar 14 is manipulated mistakenly during operation of the micro motion switch 8, the drive instruction circuit 36 of the CPU 11 may be configured to recognize both signals from the operation handle bar 14 and the micro motion switch 8 and then stop output of its signal. Therefore, the apparatus may be safely stopped automatically.

In the mobile X-ray apparatus of the present invention, when the apparatus is moved near the bed and so on, and the operator moves to the collimator 7 to aim the collimator 7 of the X-ray tube 18 at the target part of the patient, since the micro motion switch 8 for moving the apparatus slightly is placed near the collimator 7 of the X-ray tube 18, the operator does not have to go back to neighborhood of the operation handle bar 14 to adjust the direction of the collimator 7. Therefore, adjustment of the collimator 7 of the X-ray tube 18 can be carried out rapidly and examination efficiency improves.

In the mobile X-ray apparatus of the present invention, manipulation of the micro motion switch 8 can be manipulated safely because when the operation handle bar 14 is manipulated by others mistakenly during operation of the micro motion switch 8, the apparatus may be stopped automatically.

The micro motion switch 8 can also be manipulated safely because when the micro motion switch 8 is kept inclined in a direction for a given time, the drive instruction circuit 36 may stop the output of its signal and movement of apparatus can be stopped until manipulation of the micro motion switch 8 stops once.

What is claimed is:

1. A mobile X-ray apparatus for a circuit examination comprising:
    an X-ray tube with a collimator;
    a mobile base having a pair of driven wheels;
    a holder attached and movable to said base, said holder holding said X-ray tube;
    a motor driver disposed in said base, driving said wheels;
    an operation handle bar disposed in said base, providing a signal for driving said motor driver at a first speed;
    an input means, separated from said handle bar, for providing a signal for driving said motor driver at a second speed being less than the first speed;
    a controller for controlling said motor driver respectively according to said signal from said handle bar or said input means.

2. A mobile X-ray apparatus according to claim 1, wherein said input means is placed at a part which can move independently from said mobile base.

3. A mobile X-ray apparatus for a circuit examination comprising:
    an X-ray tube with a collimator;
    a mobile base having a pair of driven wheels;
    a holder attached and movable to said base, said holder holding said X-ray tube;
    a motor driver disposed in said base, driving said wheels;
    an operation handle bar disposed in said base, providing a signal for driving said motor driver;
    an input means, separated from said handle bar, for providing a signal for driving said motor;
    a controller for controlling said motor driver respectively according to said signal from said handle bar or said input means, wherein said input means is placed at said collimator which can move independently from said mobile base.

4. A mobile X-ray apparatus for a circuit examination comprising:
    an X-ray tube with a collimator;
    a mobile base having a pair of driven wheels;
    a holder attached and movable to said base, said holder holding said X-ray ray tube;
    a motor driver disposed in said base, driving said wheels;
    an operation handle bar disposed in said base, providing a signal for driving said motor driver;
    an input means, separated from said handle bar, for providing a signal for driving said motor;
    a controller for controlling said motor driver respectively according to said signal from said handle bar or said input means, wherein said input means is placed at said X-ray tube which can move independently from said mobile base.

5. A mobile X-ray apparatus for a circuit examination comprising:
    an X-ray tube with a collimator;
    a mobile base having a pair of driven wheels;
    a holder attached and movable to said base, said holder holding said X-ray tube;
    a motor driver disposed in said base, driving said wheels;
    an operation handle bar disposed in said base, providing a signal for driving said motor driver;
    an input means, separated from said handle bar, for providing a signal for driving said motor;
    a controller for controlling said motor driver respectively according to said signal from said handle bar or said input means, wherein said input means is placed at said holder which can move independently from said mobile base.

6. A mobile X-ray apparatus for a circuit examination comprising:
    an X-ray tube with a collimator;
    a mobile base having a pair of driven wheels;
    a holder attached and movable to said base, said holder holding said X-ray tube;
    a motor driver disposed in said base, driving said wheels;
    an operation handle bar disposed in said base, providing a signal for driving said motor driver;
    an input means, separated from said handle bar, for providing a signal for driving said motor;
    a controller for controlling said motor driver respectively according to said signal from said handle bar or said input means, wherein said controller stops motion of said mobile base when receiving a signal from said handle bar during receiving a signal from said input means.

7. A mobile X-ray apparatus for a circuit examination comprising:
    an X-ray tube with a collimator;
    a mobile base having a pair of driven wheels;
    a holder attached and movable to said base, said holder holding said X-ray ray tube;
    a motor driver disposed in said base, driving said wheels;
    an operation handle bar disposed in said base, providing a signal for driving said motor driver;
    an input means, separated from said handle bar, for providing a signal for driving said motor;
    a controller for controlling said motor driver respectively according to said signal from said handle bar or said input means, wherein said input means is placed at said holder which can move independently from said mobile base and wherein said controller stops motion of said mobile base when receiving a signal from said handle bar during receiving a signal from said input means.

8. A mobile X-ray apparatus according to claim 3, wherein said controller stops motion of said mobile base when receiving a signal from said handle bar during receiving a signal from said input means.

9. A mobile X-ray apparatus according to claim 4, wherein said controller stops motion of said mobile base when receiving a signal from said handle bar during receiving a signal from said input means.

10. A mobile X-ray apparatus according to claim 5, wherein said controller stops motion of said mobile base when receiving a signal from said handle bar during receiving a signal from said input means.

11. A mobile X-ray apparatus for a circuit examination comprising:
    an X-ray tube with a collimator;
    a mobile base having a pair of driven wheels;
    a holder attached and movable to said base, said holder holding said X-ray tube;

a motor driver disposed in said base, driving said wheels;

an operation handle bar disposed in said base, providing a signal for driving said motor driver;

an input means, separated from said handle bar, for providing a signal for driving said motor;

a controller for controlling said motor driver respectively according to said signal from said handle bar or said input means, wherein said controller stops motion of said mobile base when receiving a signal from said input means over a predetermined time.

12. A mobile X-ray apparatus for a circuit examination comprising:

an X-ray tube with a collimator;

a mobile base having a pair of driven wheels;

a holder attached and movable to said base, said holder holding said X-ray tube;

a motor driver disposed in said base, driving said wheels;

an operation handle bar disposed in said base, providing a signal for driving said motor driver;

an input means, separated from said handle bar, for providing a signal for driving said motor;

a controller for controlling said motor driver respectively according to said signal from said handle bar or said input means, wherein said input means is placed at said holder which can move independently from said mobile base and wherein said controller stops motion of said mobile base when receiving a signal from said input means over a predetermined time.

13. A mobile X-ray apparatus according to claim 3, wherein said controller stops motion of said mobile base when receiving a signal from said input means over a predetermined time.

14. A mobile X-ray apparatus according to claim 4, wherein said controller stops motion of said mobile base when receiving a signal from said input means over a predetermined time.

15. A mobile X-ray apparatus according to claim 5, wherein said controller stops motion of said mobile base when receiving a signal from said input means over a predetermined time.

16. A mobile X-ray apparatus according to claim 6, wherein said controller stops motion of said mobile base when receiving a signal from said input means over a predetermined time.

17. A mobile X-ray apparatus according to claim 7, wherein said controller stops motion of said mobile base when receiving a signal from said input means over a predetermined time.

18. A mobile X-ray apparatus according to claim 8, wherein said controller stops motion of said mobile base when receiving a signal from said input means over a predetermined time.

19. A mobile X-ray apparatus according to claim 9, wherein said controller stops motion of said mobile base when receiving a signal from said input means over a predetermined time.

20. A mobile X-ray apparatus according to claim 10, wherein said controller stops motion of said mobile base when receiving a signal from said input means over a predetermined time.

21. A mobile X-ray apparatus according to claim 11, wherein said predetermined time is 10 seconds to 20 seconds.

22. A mobile X-ray apparatus according to claim 12, wherein said predetermined time is 10 seconds to 20 seconds.

23. A mobile X-ray apparatus according to claim 20, wherein said predetermined time is 10 seconds to 20 seconds.

* * * * *